US008796286B2

(12) United States Patent
Choi et al.

(10) Patent No.: US 8,796,286 B2
(45) Date of Patent: Aug. 5, 2014

(54) AGENT FOR TREATMENT OF LIVER DISEASES CONTAINING PYRAZOLOPYRIMIDINONE DERIVATIVE

(75) Inventors: Seul Min Choi, Suwon-Si (KR); Byong Ok Ahn, Yongin-Si (KR); Moohi Yoo, Seoul (KR)

(73) Assignee: Mezzion Pharma Co., Ltd., Seoul (KR)

( * ) Notice: Subject to any disclaimer, the term of this patent is extended or adjusted under 35 U.S.C. 154(b) by 1467 days.

(21) Appl. No.: 11/916,752

(22) PCT Filed: Oct. 21, 2005

(86) PCT No.: PCT/KR2005/003526
§ 371 (c)(1),
(2), (4) Date: Dec. 6, 2007

(87) PCT Pub. No.: WO2006/132460
PCT Pub. Date: Dec. 14, 2006

(65) Prior Publication Data
US 2008/0207646 A1  Aug. 28, 2008

(30) Foreign Application Priority Data
Jun. 10, 2005  (KR) .......................... 10-2005-0050033

(51) Int. Cl.
*A61K 31/519* (2006.01)
*A61P 7/04* (2006.01)
*C07D 487/04* (2006.01)
*A61P 9/08* (2006.01)

(52) U.S. Cl.
CPC ............ *A61K 31/519* (2013.01); *C07D 487/04* (2013.01)
USPC ...................................... 514/262.1; 544/262

(58) Field of Classification Search
CPC ............................ C07D 487/04; A61K 31/519
USPC .......................................................... 514/262.1
See application file for complete search history.

(56) References Cited

FOREIGN PATENT DOCUMENTS

| EP | 1336602 A1 | 8/2003 |
|---|---|---|
| WO | 03/063875 A1 | 8/2003 |
| WO | 2004/002461 A2 | 1/2004 |
| WO | 2004/037183 A2 | 5/2004 |
| WO | 2004/108138 A1 | 12/2004 |
| WO | 2004/108662 A2 | 12/2004 |
| WO | 2006/074872 A1 | 7/2006 |

OTHER PUBLICATIONS

Robalino et. al. (see the abstract, < http://content.onlinejacc.org/cgi/content/abstract/17/2/492>, downloaded Aug. 28, 2010, pp. 1-4.*
National Institutes of Health website, < http://digestive.niddk.nih.gov/ddiseases/pubs/cirrhosis/>, downloaded Aug. 28, 2010, pp. 1-9.*
Hu et. al. (Expert Opinion Biol. Ther., 2009, 9(10), pp. 1305-1312).*
Program and Abstract for "10th Biennial Meeting of the Asia Pacific Society for Sexual Medicine", Oct. 4-8, 2005, cover and ppl, 10-12,, 32, 33.*
Makisalo et. al. (Liver Transplantation, 2004, 10(7), pp. 945-950).*
Francis J. Eng, et al., Fibrogenesis I. New Insights into Hepatic Stellate . . ., American Journal of Physiology Gastrointestinal Liver Physiology, vol. 279(1), pp. G7-G11, 2000.
Marie-Reine Losser, et al., Mechanisms of Liver Damage, Seminars in Liver Disease, vol. 16(4), pp. 357-367, 1996.
Anke M. B. C. Tiggelman, et al., Transforming Growth Factor-B-Induced Collagen . . . , Journal of Hepatology, vol. 26, pp. 1220-1228, 1997.
David A. Brenner, et al., Type I Collagen Gene Regulation and the Molecular . . . , American Journal of Physiology, vol. 264(4 Pt 1), pp. G589-G595, 1993.
Pere Gines, et al., Management of Cirrhosis and Ascites, New England Journal of Medicine, vol. 350, pp. 1646-1654, 2004.
Don C. Rockey, Hepatic Blood Flow Regulation by Stellate Cells . . . , Seminars in Liver Disease, vol. 21(3), pp. 337-349, 2001.
Jeanine Trevillyan, et al., Management of Portal Hypertension and Esophageal . . . , American Family Physician, vol. 55(5), pp. 1851-1858, 1997.
Isabelle Colle, et al., Systemic and Splanchnic Haemodynamic Effects of . . . , Liver International, vol. 24(1), pp. 63-68, 2004.
Isabelle Colle, et al., Sildenafil in Rats with Cirthosis and Portal Hypertension: Systemic . . . , Digestive Diseases Week, Abstract S1553, 2003.
P. Zapater, et al., Pharmacokinetic Variations of Acetaminophen . . . , Alimentary Pharmacology Therapeutics, vol. 20 (1), pp. 29-36, 2004.
R. Kumar, et al., Pharmacokinetics of Omeprazole in Patients . . . , Methods and Findings in Experimental and Clinical Pharmacology, vol. 25(8), pp. 625-630, 2003.
K. Kotzampassi, et al., Sustainable Reduction of Portal Pressure . . . , Hepatology Research, vol. 19(2), pp. 108-119, 2001.
Han-Chieh Lin, et al., Effects of Substained-release Lanreotide on Hemodynamics . . . , Journal of Hepatology, vol. 31 (3), pp. 482-488, 1999.
KK. Kang, et al., DA-8159, A Potent CGMP Phosphodiesterase Inhibitor, Attenuates . . . , Archives of Pharmacal Research, vol. 26(8), pp. 612-619, 2003.
KK. Kang, et al., DA-8159, A New PDE5 Inhibitor, Attenuates the Development of . . . , Journal of International Medical Research, vol. 31(6), pp. 517-528, 2003.

* cited by examiner

*Primary Examiner* — Susanna Moore
(74) *Attorney, Agent, or Firm* — Lucas & Mercanti, LLP

(57) ABSTRACT

The present invention relates to the pharmaceutical composition for prevention and treatment of liver diseases containing pyrazolopyrimidine derivative as an active ingredient. According to the present invention, pyrazolopyrimidine derivative has an excellent effect on inhibiting collagen synthesis in hepatic stellate cells and acts directly on the portal vein. Particularly, it may increase the diameter and the amount of blood flow of the portal vein, and finally decrease the pressure thereof. Therefore, pyrazolopyrimidine derivative can be used advantageously for prevention and treatment of hepatic fibrosis, liver cirrhosis caused by hepatic fibrosis, portal hypertension and various complications caused by portal hypertension. In addition, pyrazolopyrimidine derivative according to the present invention can reduce dosing frequency because of its long half-life, and therefore, has an advantage to improve the drug compliance of patients suffering from chronical liver diseases.

4 Claims, 1 Drawing Sheet

AGENT FOR TREATMENT OF LIVER DISEASES CONTAINING PYRAZOLOPYRIMIDINONE DERIVATIVE

CROSS-REFERENCE TO RELATED APPLICATIONS

This application is filed under 35 U.S.C. §371 of PCT/KR2005/003526, filed on Oct. 21, 2005, which claims the benefit of Korean Patent Application No. 10-2005-0050033 filed on Jun. 10, 2005, the contents of each of which are incorporated herein by reference.

TECHNICAL FIELD

The present invention relates to a pharmaceutical composition for the prevention and treatment of liver disease containing pyrazolopyrimidinone derivative as an active ingredient, more precisely, a pharmaceutical composition for the prevention and treatment of hepatic fibrosis, liver cirrhosis caused by hepatic fibrosis, portal hypertension and various complications led by portal hypertension containing pyrazolopyrimidinone derivative as an active ingredient.

BACKGROUND ART

The liver has more biochemical functions than any other organ. It is an essential organ through which absorbed food, medicine and other foreign materials are passed, and the liver has a function of eliminating acquired or innate toxic materials after transforming those toxic materials into water-soluble form. And, it is generally involved in the metabolic functions of various organs. The liver tissues synthesize and supply essential proteins such as albumin for the human body, and at the same time, generate and discharge active materials in vivo. As explained above, the liver is a crucial organ controlling human metabolic functions, in which numerous chemical processes take place. It has been confirmed so far that approximately 500 chemical processes occur in the liver in a short period of time. Hepatocytes are the chief functional cells of the liver, and each individual hepatocyte is 15-30 micron in diameter. The human liver contains approximately 250 billion hepatocytes.

Damage to hepatocytes results in necrosis of the cells. After necrosis, however, hepatocytes are regenerated owing to their excellent innate regeneration ability. Nevertheless, repetition of necrosis and regeneration triggers hepatic fibrosis, and as a result, hepatic cirrhosis, portal hypertension and complications thereby occur.

A series of related diseases all develop after hepatic fibrosis. Hepatic fibrosis is caused by the accumulation of collagen, a fibrogenic substance, in the liver. Liver cells are composed of hepatocytes, sinusoidal endothelial cells (SEC), Kupper cells, and hepatic stellate cells (HSC), and among these 4 types of cells, hepatic stellate cells play the most important role in hepatic fibrosis (*American Journal of Physiology. Gastrointestinal & Liver Physiology,* 279(1), G7, 2000). Hepatic stellate cells comprise 15% of total liver cells and normally have a function of storing retinoid which is a vitamin A precursor. However, once hepatocytes are damaged, Kupper cells begin to consume the damaged hepatocytes and secrete cytokines (TGF-beta, PDGF, FGF, HGF, PAF and ET-1) to proliferate hepatic stellate cells. The hepatic stellate cells are differentiated into myofibroblasts. Myofibroblasts synthesize collagen, which accumulates in extracellular matrix and leads to hepatic fibrosis. This means the activation of hepatic stellate cells plays an essential role in the development of hepatic fibrosis.

More precisely, the activation of hepatic stellate cells is accomplished in the three following stages—pre-inflammatory stage, inflammatory stage, and post-inflammatory stage.

In the pre-inflammatory stage, hepatocyte damage induces the secretion of wound hormone, a stimulator of hepatic stellate cell proliferation, or proliferation of hepatic stellate cells by reducing arginase, an inhibitor of the cell proliferation. In most cases, alcohol causes the generation of acetaldehyde or lipid peroxide, resulting in the promotion of a matrix gene expression.

In the inflammatory stage, hepatic stellate cells are proliferated by cytokines (TGF-beta, PDGF, FGF, HGF, PAF and ET-1) secreted in the activated Kupper cells and platelets, which are then differentiated into myofibroblasts able to generate fibrocytes (*Seminars in Liver Disease,* 16(4), 357, 1996; *Journal of Hepatology,* 26(6), 1220, 1997).

In the post-inflammatory stage, cytokines and growth factors are secreted in completely differentiated myofibroblasts to activate non-differentiated hepatic stellate cells and to secrete extracellular matrices. Myofibroblasts activated and differentiated from hepatic stellate cells synthesize collagen, which is then accumulated in extracellular matrix. Collagen monomer is very unstable and easily decomposed at body temperature, and the decomposed monomers are polymerized to induce hepatic fibrosis (*American Journal of Physiology,* 264(4 Pt 1), G589, 1993).

Hepatic cirrhosis is attributed to hepatic fibrosis, which is developed by the polymerization of the continuously accumulated collagen, changing the accumulated collagen into insoluble fiber. Hepatic cirrhosis can also be induced by continuing inflammation in the liver accompanying hepatocyte destruction, regeneration and scarring, caused by long-term alcohol abuse, hepatitis, exposure to toxic substances, etc. As a result, the size of the liver is reduced and the surface of the liver becomes bumpy. Severe hepatic cirrhosis is a serious disease causing lethal complications such as portal hypertension, hemorrhage (especially in esophagus and stomach), hepatoma, intoxication by the accumulation of waste matters, coma, etc (*N. Engl. J. Med.* 350:1646-1654).

Portal hypertension is closely related to the activation of hepatic stellate cells, hepatic fibrosis and hepatic cirrhosis. Myofibroblasts differentiated by the activation of hepatic stellate cells reduce hepatocyte elasticity, and so intrahepatic resistance increases and portal hypertension is developed (*Semin Liver Dis* 2001; 21:337-349).

Unlike other organs, liver tissue characteristically has a double pathway of blood flow, which is arterial blood with plenty of oxygen flows into liver tissue through the hepatic artery, and venous blood containing nutrients absorbed from stomach or intestines flows in through the hepatic portal vein. The amount of blood flowing in through the hepatic artery is about 400 ml per minute, and the amount of blood flowing in through the hepatic portal vein is about 1200 ml per minute, meaning that ¼ of total blood flowing into the liver takes the road of hepatic artery, while the remaining ¾ takes the road of hepatic portal vein.

Portal blood pressure, similar to other venous pressure, is only about ⅒ of arterial pressure, and this can easily lead to disorders in blood circulation. The repetition of damage to and regeneration of hepatocytes by continuing inflammation results in the accumulation of fibrous materials and the development of regeneration nodes. Regeneration nodes put pressure on the pathway of blood in liver tissue or constrict the blood vessel itself, causing blood circulatory disturbance. While blood flow through the portal vein is not changed, blood flow through liver tissue is decreased by the disorder in blood circulation. As a result, portal blood pressure is increased, causing portal hypertension. The portal vein is a kind of vein without antireflux valve, so blood reflux can occur any time portal blood pressure is increased by circulation disorder, and then the blood seeks a detour in circulation. As a result, collateral vessels in the digestive track (in particular esophagus and stomach) are developed, thereby causing hypersplenism. Collateral vessels are generally developed in low pressure areas such as submucosa of esophagus, anteriolateral abdominal wall, rectum, etc, with consequent symptoms of esophageal varix, ascitic fluid, hemorrhoids and splenic enlargement.

The most common complication of portal hypertension is esophageal varices which need at least 12 mmHg of pressure to be formed. Approximately one third of liver cirrhosis patients show varices in esophagus and stomach, which account for about 30% of causes of death (*American Family Physician*, 55(5), 1851, 1997). Until now, the factors involved in bleeding by esophageal varices and gastric varices are not fully understood, but the size of varices is believed to be associated with the severity of portal hypertension (Pharmacotherapy: a phathophysiologic approach, 1996).

To treat portal hypertension, surgical operations such as splenectomy or portacaval shunt have been performed to reduce portal bed flow. Medicaments for portal hypertension are exemplified by vasopressin generally used for acute variceal hemorrhage, somatostatin, non-specific beta-adrenergic blocker, alpha-adrenergic blocker, and nitrate preparations. These medicaments decrease portal vein pressure by reducing the arterial flow towards the liver. As a result, the whole portal blood stream to the liver, which is already badly affected, deteriorates even further. Therefore, for many years there has been a need for the development of substances which decrease the portal vein pressure selectively.

It has been proved that phosphodiesterase type-5 (hereinafter referred to as "PDE 5") inhibitor, already known as an active ingredient in medication for erectile dysfunction, is also effective in treating portal hypertension and diseases related thereto.

For example, the use of PDE 5 inhibitors for the prevention and treatment of portal hypertension is described in PCT/EP2004/006014. Precisely, PDE 5 inhibitors, sildenafil and vardenafil, have preventive and therapeutic effects on portal hypertension and its complications by lowering portal blood pressure through increasing the diameter of the portal blood vessel and portal blood flow.

However, relaxation of the portal vein does not automatically mean the increase of blood flow through the liver and the decrease of portal blood pressure, and in fact, the effect of a specific PDE 5 inhibitor on blood flow through the liver and portal blood pressure is unpredictable.

According to an earlier report investigating the effect of sildenafil on systemic and visceral hemodynamics in experimental cirrhosis models, sildenafil reduces average arterial pressure, causing systemic hypotension, and increases blood flow through mesenteria and portal blood pressure dose-dependently (*Liver International*, 24(1), 63, 2004; *Digestive Disease Week*, Abs S1553, 2003). Thus, the researchers who performed the above experiments concluded that additional studies are required to prescribe sildenafil to a cirrhosis patient, because the increase of portal blood pressure by sildenafil might bring bleeding complications.

In the case of liver cirrhosis, splanchnic vascular relaxation by over-production of local NO is observed. According to a report, sildenafil increases the effect of NO, resulting in the decrease of angiomesenteric tonicity and the increase of portal blood flow (*Liver International*, 24(1):63, 2004; *Digestive Disease Week*, Abs S1553, 2003).

More or less, metabolic function of liver is reduced in patients with liver disease such as liver cirrhosis, portal hypertension, etc, so that the area under the concentration-time curve (AUC) and the half-life of medicament is increased (*Alimentary Pharmacology Therapeutics*, 20(1), 29, 2004; *Methods and Findings in Experimental and Clinical Pharmacology*, 25(8), 625, 2003).

Nevertheless, a patient with chronic liver disease needs long-term administration and multiple prescriptions. If the patient is prescribed medicine having a short half-life, it lowers the rate of patient compliance and hinders effective treatment.

Therefore, studies have been undertaken to prepare a medicine for the treatment of chronic liver disease that maintains its pharmaceutical effect continuously, and increases the rate of patient compliance. And it was reported that when synthetic somatostatin-like octreotide was administered once a day as a sustained release preparation, the effect of reducing portal blood pressure was long lasting (Hepatology Research, 19(2), 108, 2001). Furthermore, when sustained release lanreotide was administered once a day by intramuscular injection to a mouse with portal hypertension induced by hepatoportal sclerosis, peripheral vasodilation and excessive blood circulation were postponed and portal hypertension and visceral congestion, in addition to portal-systemic shunt, were prevented (*Journal of Hepatology*, 31(3), 482, 1999).

Considering the above problems, there is a need to develop a novel medicine that can increase hepatic blood flow without side effects, reduce portal blood pressure, and increase compliance with long half-life.

The present inventors synthesized a novel compound, pyrazolopyrimidinone derivative 5-[2-propyloxy-5-(1-methyl-2-pyrollidinylethylamidosulphonyl) phenyl]-1-methyl-propyl-1,6-dihydro-7H-pyrazolo(4,3-d)pyrimidin-7-one, and reported its PDE 5 inhibiting effect in a previous study (Korean Patent No. 377,782). Then, the present inventors kept studying on pyrazolopyrimidinone derivative, as a PDE 5 inhibitor, and completed this invention by confirming that the pyrazolopyrimidinone derivative has excellent collagen synthesis inhibitory effect, and can enhance medicinal compliance of chronic liver disease patients since pyrazolopyrimidinone derivative has a long half-life and reduces portal blood pressure.

DISCLOSURE OF INVENTION

Technical Problem

It is an object of the present invention to provide a pharmaceutical composition for prevention and treatment of liver disease containing pyrazolopyrimidinone derivative as an active ingredient.

It is another object of the present invention to provide a hepatic fibrosis inhibitor.

It is a further object of the present invention to provide a pharmaceutical composition for prevention and treatment of hepatic cirrhosis by inhibiting hepatic fibrosis.

It is also an object of the present invention to provide a portal hypertension inhibitor.

It is another object of the present invention to provide a pharmaceutical composition for prevention and treatment of complications generated by the progress of portal hypertension.

Technical Solution

To achieve the above objects, the present invention provides a pharmaceutical composition for prevention and treatment of hepatic fibrosis, liver cirrhosis, portal hypertension, and the complications caused thereby, containing pyrazolopyrimidinone derivative as an active ingredient.

Hereinafter, the present invention is described in detail.

The present invention provides a pharmaceutical composition for the prevention and treatment of hepatic fibrosis, liver cirrhosis, portal hypertension, and the complications caused thereby, containing pyrazolopyrimidinone derivative (5-[2-propyloxy-5(1-methyl-2-pyrollidinylethylamidosulphonyl)phenyl]-1-methyl-propyl-1,6-dihydro-7H-pyrazolo(4,3-d)pyrimidin-7-one) represented by the following Formula I as an active ingredient.

Formula I

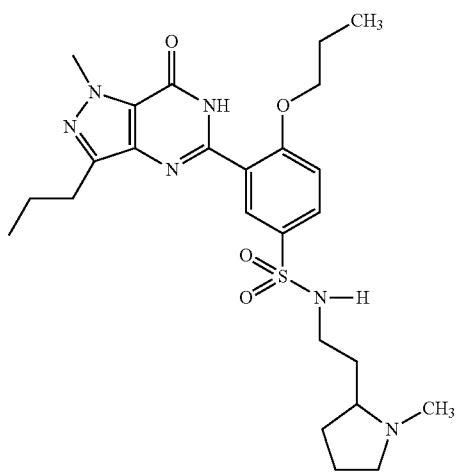 [SMILES: CCCOc1ccc(S(=O)(=O)NCCC2CCCN2C)cc1-c1nc2c(CCC)nn(C)c2c(=O)[nH]1]

Pyrazolopyrimidinone derivative is a kind of PDE 5 inhibitor. It has excellent PDE 5 inhibitory activity and selectivity. Pyrazolopyrimidinone derivative is absorbed fast owing to its enhanced solubility, and has high bioavailability and huge biodistribution. Furthermore, it is characterized by at least three-fold longer half-life than those of sildenafil and vardenafil.

The physicochemical properties of pyrazolopyrimidinone derivative are as follows; it is insoluble in water but soluble in acetic acid, methanol and chloroform. Its melting point is at 158-161° C. and it has $pKa_1$ and $pKa_2$ values of 6.5 and 12.5 respectively. It is a white or pale yellow powder which is not hydrate or solvate either.

Pyrazolopyrimidinone derivative can be synthesized by following three steps, as particularized below:

In step 1, 4-[2-propyloxy-5-(chlorosulfonyl)benzamido]-1-methyl-3-propyl-5-carbamoyl pyrazole is prepared. Precisely, the proper amount of 4-[2-propyl-oxy benzamido]-1-methyl-3-propyl-5-carbamoyl pyrazole is added to the solution of the proper amount of chlorosulfonic acid cooled at 0° C. The mixture is stirred, filtered, washed and dried to give 4-[2-propyloxy-5-(chlorosulfonyl)benzamido]-1-methyl-3-propyl-5-carbamoyl pyrazole.

In step 2, 4-[2-propyloxy-5-(1-methyl-2-pyrrolidinylethyl ami-dosulfonyl)benzamido]-1-methyl-3-propyl-5-carbamoyl pyrazole is prepared from the pyrazole compound produced in the above step 1. Precisely, the proper amount of 2-(2-aminoethyl)-1-methylpyrrolidine is added at 0° C. to dichloromethane solution containing the proper amount of 4-[2-propyloxy-5-(chlorosulfonyl)benzamido]-1-methyl-3-propyl-5-carbamoyl pyrazole of step 1, followed by stirring. Upon completion of reaction, the reaction solution is diluted with dichloromethane. The organic layer is washed, dried, concentrated and filtered to give 4-[2-propyloxy-5-(1-methyl-2-pyrrolidinylethyl amidosulfonyl)benzamido]-1-methyl-3-propyl-5-carbamoyl pyrazole.

In step 3, 5-[2-propyloxy-5-(1-methyl-2-pyrrolidinylethyl amidosulfonyl)phenyl]-1-methyl-3-propyl-1,6-dihydro-7H-pyrazolo(4,3-d)pyrimidin-7-one, which is pyrazolopyrimidinone derivative of the present invention, is prepared from the compound obtained in step 2. Precisely, the proper amount of pyrazole compound synthesized in step 2 is dissolved in t-butanol, to which the proper amount of potassium t-butoxide is added, followed by reflux for a required time. Upon completion of reaction, the reaction solution is cooled down, diluted, washed and dried. Then, reduced pressure distillation, elimination of a solvent and silica gel column chromatography are performed to give the novel pyrazolopyrimidinone derivative of the invention.

The present invention relates to a pharmaceutical composition for prevention and treatment of liver disease, and is described as follows.

The present invention provides a hepatic fibrosis inhibitor. 2) The present invention also provides a pharmaceutical composition for prevention and treatment of hepatic cirrhosis inhibiting hepatic fibrosis. 3) The present invention further provides a portal hypertension inhibitor. 4) The present invention also provides a pharmaceutical composition for prevention and treatment of complications caused by portal hypertension.

With the increase of collagen deposit in hepatic stellate cells in the liver, hepatic fibrosis is developed. Then, the liver cells remaining between fibers begin to proliferate to maintain the liver functions, by which regeneration nodes are formed. The central vein of the hepatic lobule is pressed by such fibrosis and regeneration nodes, resulting in the block of blood flow through the portal vein into liver, causing portal hypertension.

Thus, portal blood pressure might be reduced with the inhibition of hepatic fibrosis. Blood flow through the liver can be enhanced with the decrease of portal blood pressure and the increase of portal blood flow, leading to the protection of the liver.

As mentioned hereinbefore, control of hepatic fibrosis and portal blood pressure is closely related to liver protection. The composition of the present invention containing pyrazolopyrimidinone derivative as an active ingredient can prevent the progress of hepatic fibrosis by inhibiting collagen synthesis in hepatic stellate cells, has a protective effect on the liver, can reduce portal blood pressure by working directly towards the portal vein, and increases blood flow through the portal vein, all suggesting that the present invention has an excellent therapeutic effect on chronic liver disease related to hepatic fibrosis and portal hypertension.

Pyrazolopyrimidinone derivative of the present invention has 10-16 times as excellent collagen synthesis inhibitory effect as other conventional PDE 5 inhibitors. It was confirmed by such excellent effect that pyrazolopyrimidinone derivative of the invention can inhibit hepatic fibrosis caused by the deposit of collagen in hepatic stellate cells in the liver, and protect the liver (see Table 1). In addition, pyrazolopyrimidinone derivative of the invention reduces portal blood pressure dose-dependently but increases portal diameter and portal blood flow. Unlike sildenafil which was reported to rather increase portal blood pressure, pyrazolopyrimidinone derivative of the invention can be effectively used for the treatment of portal hypertension and various complications induced thereby (see Table 2).

Chronic liver disease includes various complications caused by liver cirrhosis resulting from hepatic fibrosis and portal hypertension (Rubin Farber Pathology, 1999). Such complications are exemplified by esophageal varices (*American Family Physician,* 55(5), 1851, 1997), splenic enlargement and hypersplenism, ascites, hepatorenal syndrome (Gastroenterology Vol. 120, No. 3), spontaneous bacterial peritonitis (*Curr Opinion In Gastroenterology* 2004, 20:254-263), hepatopulmonary syndrome (*Dig Dis Sci* 2003, 48: 556-560), hepatic encephalopathy (*Neuroreport* 2003, 14:2379-2382), etc. Such complications are described in detail hereinafter.

Esophageal varices means the generation of abnormal veins in esophagus or stomach. When the condition worsens it comes worse, those veins burst and bleed. High portal blood pressure causes disturbance in blood flow, increasing the size of spleen cells, through which splenic enlargement, another cause of internal bleeding, develops. Ascites indicates abdominal dropsy. High portal pressure increases hydrostatic pressure in blood plasma and lymph, resulting in lymphatic stasis inducing outflow of moisture into the abdominal cavity. The ascites pressure the lung, causing labored respiration, and long-term pressure on the lung even causes fatal sepsis. Idiopathic (autogenous) bacterial peritonitis, also triggered by high portal blood pressure, is often observed in patients with ascites, unlike other peritonitis (secondary peritonitis) which has an anticipatory cause such as internal enterrohexis and gastrorrhexis or trauma. Hepatorenal syndrome indicates severe depression of the kidney by hepatic cirrhosis, triggered by an imbalance of body fluid. Hepatopulmonary syndrome is a disease of hypoxia, observed in patients with chronic liver disease, although those patients do not have a specific heart or lung disease. Like hepatic cirrhosis, hepatic encephalopathy is another severe complication that develops from mal-function in the conversion of ammonia, an internal toxic material, into urea as liver functions decline, thereby affecting the neuronal system and even leading to fatal coma.

As explained hereinbefore, the disturbance in blood circulation pressures portal veins and then the reflux of blood occurs in portal veins, so the blood flow finds a de-tour without passing through the liver. As a result, collateral vessels are generated particularly in low pressure areas of the alimentary tract such as under the mucous layer of the esophagus, on anteriolateral abdominal walls and in the rectum, etc. Thus, pyrazolopyrimidinone derivative of the present invention can be effectively used as a pharmaceutical composition for prevention and treatment of the above mentioned complications by fundamentally suppressing the increasing portal pressure.

A pharmaceutical composition for the prevention and treatment of liver disease, containing pyrazolopyrimidinone derivative as an active ingredient of the present invention, can be administered orally or parenterally and be used in general forms of pharmaceutical formulation. In this invention, oral administration is preferred. The pharmaceutical composition of the present invention can be prepared for oral or parenteral administration by mixing with generally used fillers, extenders, binders, wetting agents, disintegrating agents, diluents such as surfactant, or excipients.

Solid formulations for oral administration are tablets, pills, dusting powders, granules and capsules. These solid formulations are prepared by mixing one or more suitable excipients such as starch, calcium carbonate, sucrose, lactose, gelatin, etc. Except for the simple excipients, lubricants, for example magnesium stearate, talc, etc, can be used.

Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, Laurin butter, glycerogelatin, etc.

The effective dosage of the composition containing pyrazolopyrimidinone derivative as an active ingredient of the present invention can be determined according to weight, age, gender, health condition, diet, administration frequency, administration method, excretion and severity of a disease. The preferable dosage and administration frequency for an adult are 50-200 mg per day and once to three or four times a day.

BEST MODE FOR CARRYING OUT THE INVENTION

Figure 1:
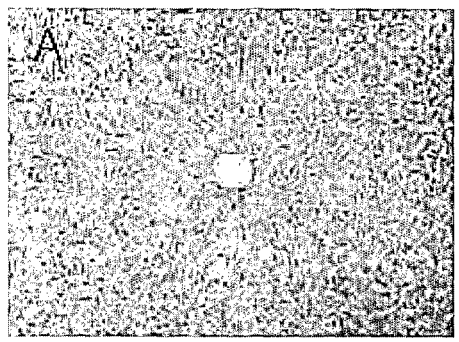
FIG. 1-4 is a set of photomicrographs showing the collagen synthesis inhibitory effects, according to Example 2 of the invention, of wild type control (FIG. 1), solvent control (FIG. 2), sildenafil treated group (FIG. 3) and pyrazolopyrimidinone derivative treated group (FIG. 4).
Figure 2:
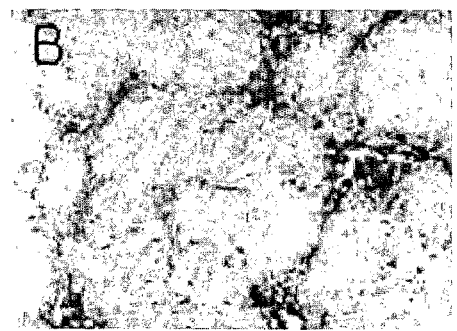
Figure 3:
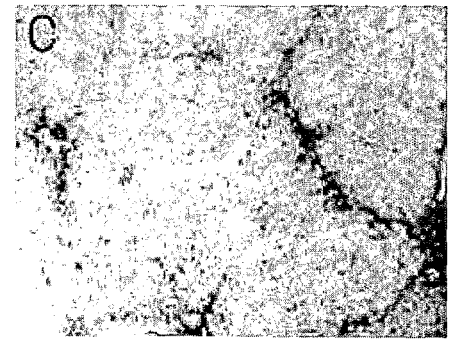
Figure 4:
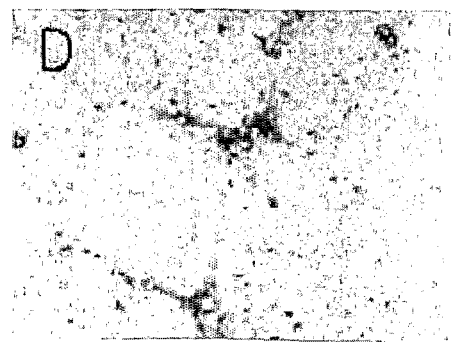

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Investigation of Inhibitory Effect of Pyrazolopyrimidinone Derivative on Collagen Synthesis Using Hepatic Stellate Cells The following experiments were performed to investigate the inhibition effect of pyrazolopyrimidinone derivative of the present invention on collagen synthesis.

Hepatic stellate cells were isolated from Sprague Dawley white male rats (about 300 g in weight, n=10). First, ketamin was injected into the abdominal cavity to anesthetize the rats. The abdomen was opened and heparin was injected into the portal vein. Then, Hank's buffer solution containing 0.02% pronase and 0.015% collagenase was perfused through the liver for a required time to prepare liver in sections. The extracted liver was crushed on a sterilized petri-dish, then put in a buffer solution containing pronase and DNase, and the crushed liver was then homogenized on a sterilized petri-dish.

The prepared sample was filtered with 100 μm nylon mesh in a 50 mL tube. Centrifugation was performed with 50 g for 2 minutes to separate nonparenchymal cells in supernatant. Centrifugation was performed again with 450 g at 4° C. for 10 minutes. The precipitate was floated in a buffer solution containing 25 μg/mL of DNase, followed by centrifugation with 450 g at 4° C. for 10 minutes, which was repeated twice. The final precipitate was floated in 21 mL of buffer solution, which was then mixed with 17 mL of 25% OptiPrep to prepare the final solution of 11.2% OptiPrep (1.058 cm$^3$). Cell suspension solution mixed with OptiPrep was carefully distributed into four 15 mL tubes containing 3 mL of 17% OptiPrep, to which 1 mL of buffer solution was added. Centrifugation was performed with 1400 g at 4° C. for 17 minutes, and as a result, pure hepatic stellate cells were obtained from the opaque layer between the buffer solution and 11.8% OptiPrep.

The separated hepatic stellate cells were suspended in DMEM (Dulbecco's Modified Eagle' Media), followed by washing. The cells were suspended again in DMEM supplemented with 10% FBS (Fetal Bovine Serum) and antibiotics, then inoculated into a culture vessel, which was cultured in a 37° C. 5% $CO_2$ incubator. The culture medium was first replaced 24 hours later, and then replaced every 48 hours for sub-culture.

Hepatic stellate cells sub-cultured 8 times were grouped by $2 \times 10^5$, which were pre-treated with 25 ng/mL of PDGF (Platelet Derived Growth Factor) for 24 hours. At that time, pyrazolopyrimidinone derivative, sildenafil and vardenafil were added at different concentrations of 0, 3, 5, and 10 ng/mL for reaction. The total RNA was extracted and RT-PCR (Reverse Transcriptase Polymerase Chain Reaction) for collagen was performed.

Based on the relative concentration to beta-actin, a target material was compared with other test samples. In order to determine the inhibitory effect of a target sample on collagen synthesis, inhibitory concentration 50% ($IC_{50}$) was investigated, and the result is shown in Table 1.

TABLE 1

Inhibitory effect of PDE 5 inhibitors on collagen synthesis.

| | Pyrazolopyrimidinone derivative | Sildenafil | Vardenafil |
|---|---|---|---|
| $IC_{50}$ (nM) | $0.8 \pm 0.2^a$ | $13.1 \pm 2.3$ | $7.8 \pm 1.7$ |

$^a$Mean ± Standard Deviation

As shown in Table 1, $IC_{50}$ of pyrazolopyrimidinone derivative was 0.8±0.2 nM, which was 16 times and 10 times higher collagen synthesis inhibitory effect than those of sildenafil and vardenafil, respectively. Therefore, it was confirmed that pyrazolopyrimidinone derivative of the present invention has more excellent collagen synthesis inhibitory effect than other PDE 5 inhibitors, sildenafil and vardenafil, and accordingly it has also excellent inhibitory effect on hepatic fibrosis resulting from excessive collagen deposit, and excellent liver protective effect thereby.

Example 2

Investigation of Liver Protective Effect of Pyrazolopyrimidinone Derivative Using Hepatic Fibrosis Animal Model The following experiments were performed to investigate the in vivo collagen synthesis inhibitory effect of pyrazolopyrimidinone derivative of the present invention.

Sprague Dawley white female rats (having approximately 300 g in weight) were divided into 4 groups (5 rats per group), and hepatic fibrosis was induced in experimental groups except the wild type control group (Toxicology, 2001). DMN (dimethylnitrosamine) was injected into the abdominal cavity in a dose of 10 mg/kg serially for 2 weeks with a dose frequency of three times per week. Pyrazolopyrimidinone derivative and sildenafil in triazole buffer (Merch) were orally administered at 10 mg/kg/day for 2 weeks (DMN inducing period). Only triazole buffer was administered to the solvent control group. Two weeks later, the liver was extracted, fixed in 10% neutral formalin, embedded in paraffin and sliced by 4 m. Each section was treated with xylene to eliminate paraffin, followed by treatment with alcohol and 0.1% hydrogen peroxide ($H_2O_2$). After treatment with PBS, the sections were treated with polyclonal antiserum (Chemicon) against collagen type I diluted by 1:500 and polyclonal antiserum (Bio-Genesis) against collagen type III diluted by 1:100, at 37° C. for one hour. After washing, samples were treated with 1:200 diluted biotin-conjugated goat anti-rabbit IgG. Immunohistological staining was performed by reacting the samples with avidin-biotin complex (Vector Laboratories), then antigen-antibody complex was marked with 3-amino-9-ethylcarbazole (AEC), whose image was taken by optical microscope now shown in FIG. 1-4. The control group was treated with non-immunized horse serum instead of primary antibody.

As shown in FIG. 1-4, a high level of collagen synthesis was observed in hepatic portal veins and around the portal veins of the solvent control group, compared with wild type animals, indicating that collagen synthesis is remarkably inhibited by pyrazolopyrimidinone derivative and sildenafil. The inhibition of collagen synthesis in the pyrazolopyrimidinone derivative treated group was greater than that in the sildenafil treated group.

Example 3

Investigation of the Effect of Pyrazolopyrimidinone Derivative with Portal Hypertension Animal Models The following experiments were performed to investigate the effect of pyrazolopyrimidinone derivative on portal hypertension.

12 beagle dogs weighing about 10 kg were divided into four groups (3 dogs were chosen per group randomly), and bile duct ligation was performed on them. For two weeks from the operation, pyrazolopyrimidinone derivative, sildenafil and vardenafil were orally administered in doses of 10 mg/kg/day and 3 of them were administered with only solvent. The animals were fasted for 4 hours, then pentobarbital was intravenously injected to anesthetize them. A tube was inserted through the mesenteric vein to the portal vein to measure portal blood pressure.

Doppler ultrasonography was also performed to measure the diameter of portal vein. Blood flow through the portal vein was measured by using the following mathematical chemistry FIG. 1, and the result is shown in Table 2.

$$\text{Blood Flow Rate} = \pi R^2 \times V \times 60 \left(R: \frac{\text{portal vein diameter}}{2}, \right.$$

Math FIG. 1

$V$:average blood flow velocity)

TABLE 2

The effect of pyrazolopyrimidinone derivative on portal hypertension

|  | Solvent treated group | Pyrazolopyrimidinone derivative treated group | Sildenafil treated group | Vardenafil treated group |
|---|---|---|---|---|
| Portal blood pressure (kPa) | 3.13 ± 0.31[a] | 2.50 ± 0.20* | 2.93 ± 0.25 | 2.87 ± 0.25 |
| Portal vein diameter (mm) | 7.07 ± 0.15 | 7.70 ± 0.26 | 7.47 ± 0.21 | 7.43 ± 0.21 |
| Blood flow rate (ml/min) | 584.26 ± 159.97 | 932.31 ± 89.83* | 754.47 ± 80.24 | 729.29 ± 83.23 |

[a]Mean ± Standard Deviation,
*Statistically significant (p < 0.05)

As shown in Table 2, portal blood pressure was 21% decreased in the pyrazolopyrimidinone derivative treated group, 7% decreased in the sildenafil treated group and 9% decreased in the vardenafil treated group, compared with that in the solvent treated control group. From the comparison of portal vein diameter, it was confirmed that the diameters of portal veins of each of the pyrazolopyrimidinone derivative, sildenafil and vardenafil treated groups were 6-9% increased, which was thought not statistically significant. Blood flow rates through portal veins were also compared. As a result, blood flow rate in the pyrazolopyrimidinone derivative treated group was 59.9% increased, compared with that in the solvent treated group, and blood flow rates in sildenafil and vardenafil treated groups were 29.1% and 24.8% increased respectively.

From the above results, it was confirmed that pyrazolopyrimidinone derivative of the present invention, unlike sildenafil which is known to rather increase portal blood pressure, markedly reduces portal blood pressure but significantly increases blood flow through the portal vein, making it a very effective candidate for a therapeutic pharmaceutical composition for portal hypertension and complications thereof, without side effects including esophageal varix hemorrhage, etc.

Example 4

Investigation of In Vivo Pharmacokinetics of Pyrazolopyrimidinone Derivative

Nine volunteers among portal hypertension patients who were in the criterion of age from 19-45 and weight over 45 kg (within 15% deviation of ideal body weight) participated in experiments. They were all volunteers who agreed in writing to join the experiments and were trustworthy, cooperative and willing to follow the rules. They were divided into three groups randomly; three of them were administered with pyrazolopyrimidinone derivative, three with sildenafil and the remaining three were administered with vardenafil at different concentrations of 100, 50, and 10 mg, respectively.

A double blind method was used for the experiments. At 8-9 am on the test day, test medicines were given with 240 mL of water to volunteers. For 4 hours from the administration, they were fasted, and lunch was provided 4 hours later and dinner was provided 9 hours later. Blood samples were taken before the administration on the test day and at the 0.5th, 1st, 1.5th, 2nd, 2.5th, 3rd, 4th, 5th, 6th, 8th, 12th, 24th and 32nd hour after the administration. Blood plasma was isolated, followed by HPLC. 100 µL of 0.1 M sodium carbonate and 1.0 mL of ethyl ether were added to 0.5 mL of blood plasma, then mixed well for 1 minute, followed by centrifugation at 12,000 rpm for 3 minutes. Supernatant was obtained and organic solvent was volatilized using speed vac. Then, 100 µL of moving phase was added, followed by stirring. The resultant product was injected in an injector of HPLC, and the result is shown in Table 3.

TABLE 3

Comparison of half-lifes of pyrazolopyrimidinone derivative, sildenafil and vardenafil in patients with portal hypertension

|  | Pyrazolopyrinidine derivative (100 mg) | Sildenafil (50 mg) | Vardenafil (10 mg) |
|---|---|---|---|
| Half-life (hour) | 15.1 ± 3.5[a] | 4.5 ± 1.2 | 6.3 ± 2.1 |

[a]Mean ± Standard Deviation

As shown in Table 3, the half-life of pyrazolopyrimidinone derivative was 15.1±3.5 hours, which was three fold and two fold longer than those of sildenafil (4.5±1.2) and vardenafil (6.3±2.1), respectively.

Thus, pyrazolopyrimidinone derivative of the present invention not only has an excellent therapeutic effect on hepatic fibrosis and portal hypertension, but also reduces administration frequency owing to its longer half-life than other PDE-5 inhibitors, suggesting that pyrazolopyrimidinone derivative can enhance compliance in patients with chronic liver disease.

Preparative examples of the composition of the present invention are described hereinafter Preparative Example Preparation of Pharmaceutical Compositions for Oral Administration

| 1. | Preparation of powders | |
|---|---|---|
|  | Pyrazolopyrimidinone derivative | 2 g |
|  | Lactose | 1 g |

The above-mentioned ingredients were mixed together, and an airtight bag was filled with the mixture to prepare powders.

| 2. | Preparation of tablets | |
|---|---|---|
|  | Pyrazolopyrimidinone derivative | 100 mg |
|  | Corn starch | 100 mg |
|  | Lactose | 100 mg |
|  | Magnesium stearate | 2 mg |

The above-mentioned ingredients were mixed together, and tablets were prepared by tabletting according to the conventional tablet producing method.

| 3. | Preparation of capsules | |
|---|---|---|
| | Pyrazolopyrimidinone derivative | 100 mg |
| | Corn starch | 100 mg |
| | Lactose | 100 mg |
| | Magnesium stearate | 2 mg |

The above-mentioned ingredients were mixed together, and gelatin capsules were filled with the mixture to prepare capsules according to the conventional capsule producing method.

INDUSTRIAL APPLICABILITY

As explained hereinbefore, pyrazolopyrimidinone derivative of the present invention has excellent inhibitory effect on collagen synthesis in hepatic stellate cells, increases blood flow through the portal vein and expands the diameter of the portal vein by directly affecting the portal vein, and reduces portal blood pressure. Thus, pyrazolopyrimidinone derivative can be effectively used for the prevention and treatment of hepatic fibrosis, liver cirrhosis resulting from long-lasting hepatic fibrosis, portal hypertension and various complications caused therefrom. In addition, pyrazolopyrimidinone derivative of the present invention has a longer half-life in vivo, suggesting that it can enhance compliance in patients with chronic liver disease by cutting down administration frequency.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method of reducing hepatic fibrosis in a mammal comprising administering an effective amount of a pyrazolopyrimidinone having Formula I:

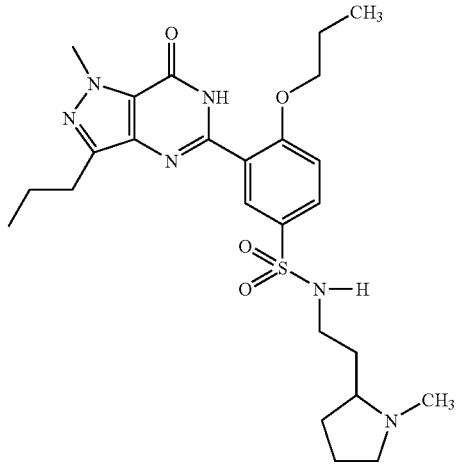 [SMILES: CCCOc1ccc(S(=O)(=O)NCCC2CCCN2C)cc1-c1nc2c(CCC)nn(C)c2c(=O)[nH]1]

to a mammal in need thereof.

2. A method of inhibiting collagen synthesis in a mammal comprising administering an effective amount of a pyrazolopyrimidinone having Formula I:

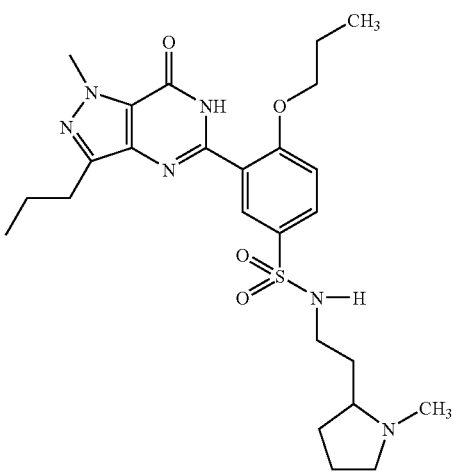 [SMILES: CCCOc1ccc(S(=O)(=O)NCCC2CCCN2C)cc1-c1nc2c(CCC)nn(C)c2c(=O)[nH]1]

to a mammal in need thereof.

3. A method for inhibiting hepatic portal hypertension in a mammal comprising administering an effective amount of a pyrazolopyrimidinone having Formula I:

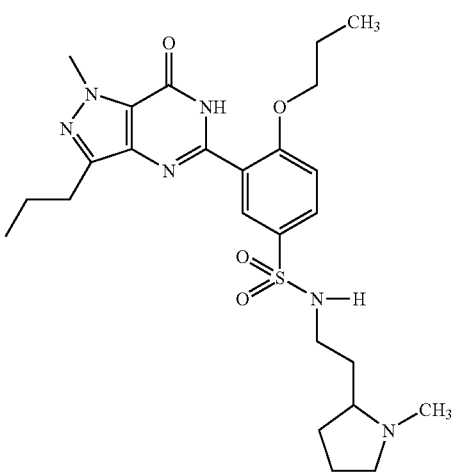 [SMILES: CCCOc1ccc(S(=O)(=O)NCCC2CCCN2C)cc1-c1nc2c(CCC)nn(C)c2c(=O)[nH]1]

to a mammal in need thereof.

4. A method for treating a complication caused by hepatic portal hypertension in a mammal comprising administering an effective amount of a pyrazolopyrimidinone having Formula I:

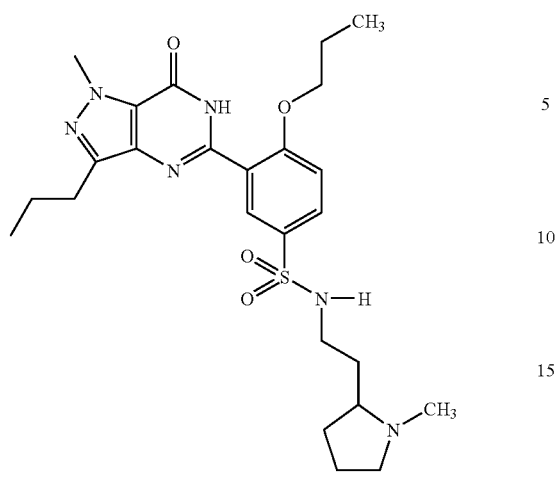
to a mammal in need thereof, wherein the complication is selected from the group consisting of esophageal varices, splenic enlargement, hypersplenism, ascites, spontaneous bacterial peritonitis, hepatorenal syndrome, hepatopulmonary syndrome and hepatic encephalopathy.
* * * * *